(12) United States Patent
Lugrís Armesto et al.

(10) Patent No.: US 11,766,348 B2
(45) Date of Patent: Sep. 26, 2023

(54) SYSTEM TO ASSIST WALKING

(71) Applicants: UNIVERSIDADE DA CORUÑA, A Coruña (ES); UNIVERSITAT POLITÈCNICA DE CATALUNYA, Barcelona (ES); UNIVERSIDAD DE EXTREMADURA, Badajoz (ES)

(72) Inventors: Urbano Lugrís Armesto, A Coruña (ES); Javier Cuadrado Aranda, A Coruña (ES); Josep Maria Font Llagunes, Barcelona (ES); Daniel Clos Costa, Barcelona (ES); Francisco Javier Alonso Sánchez, Badajoz (ES); Francisco Romero Sánchez, Badajoz (ES)

(73) Assignees: UNIVERSITAT POLITECNICA DE CATALUNYA, Barcelona (ES); UNIVERSIDADE DA CORUÑA, A Coruña (ES); UNIVERSIDAD DE EXTREMADURA, Badajoz (ES)

( * ) Notice: Subject to any disclaimer, the term of this patent is extended or adjusted under 35 U.S.C. 154(b) by 1125 days.

(21) Appl. No.: 16/342,821

(22) PCT Filed: Oct. 17, 2017

(86) PCT No.: PCT/EP2017/076482
§ 371 (c)(1),
(2) Date: Apr. 17, 2019

(87) PCT Pub. No.: WO2018/073252
PCT Pub. Date: Apr. 26, 2018

(65) Prior Publication Data
US 2019/0231573 A1    Aug. 1, 2019

(30) Foreign Application Priority Data
Oct. 17, 2016    (ES) ............................... ES201600886

(51) Int. Cl.
*A61F 5/01* (2006.01)
*A61F 2/70* (2006.01)
(Continued)

(52) U.S. Cl.
CPC .......... *A61F 5/0123* (2013.01); *A61F 5/0102* (2013.01); *A61H 3/00* (2013.01);
(Continued)

(58) Field of Classification Search
None
See application file for complete search history.

(56) References Cited

U.S. PATENT DOCUMENTS

| | | |
|---|---|---|
| 7,985,193 B2 | 7/2011 | Thorsteinsson et al. |
| 8,876,912 B2 | 11/2014 | Kampas et al. |

(Continued)

FOREIGN PATENT DOCUMENTS

| | | |
|---|---|---|
| JP | 2015-512287 A | 4/2015 |
| JP | 2016-530935 A | 10/2016 |

(Continued)

OTHER PUBLICATIONS

Eva Pröbsting et al., "Safety and walking ability of KAFO users with the C-Brace® Orthotronic Mobility System, a new microprocessor stance and swing control orthosis", May 4, 2016, Prosthetic and Orthosis International, pp. 1-13.

(Continued)

*Primary Examiner* — David H Willse
(74) *Attorney, Agent, or Firm* — SEED INTELLECTUAL PROPERTY LAW GROUP LLP

(57) ABSTRACT

The invention relates to a system to assist walking in spinal cord injured people, who preserve hip flexion capacity, comprising a pair of KAFO-type orthoses with: (a) an angular actuator (5) in each knee; (b) an orientation and acceleration sensor (6) on each leg; (c) a power supply and control system (7) to which all the sensors and actuators are connected; (d) a control algorithm deciding when to flex or extend the knee depending on the walking cycle, using information from the sensors.

7 Claims, 2 Drawing Sheets

(51) Int. Cl.
  *A61F 2/64* (2006.01)
  *B25J 9/00* (2006.01)
  *A61H 3/00* (2006.01)
  *A61F 2/76* (2006.01)

(52) U.S. Cl.
  CPC ............... *B25J 9/0006* (2013.01); *A61F 2/64* (2013.01); *A61F 2002/704* (2013.01); *A61F 2002/764* (2013.01); *A61F 2002/7625* (2013.01); *A61F 2005/0155* (2013.01); *A61H 2003/007* (2013.01)

(56) References Cited

U.S. PATENT DOCUMENTS

| | | | | |
|---|---|---|---|---|
| 2004/0116836 | A1* | 6/2004 | Kawai | B62D 57/032 600/595 |
| 2010/0125229 | A1 | 5/2010 | Rudolph et al. | |
| 2016/0206447 | A1 | 7/2016 | Auberger et al. | |

FOREIGN PATENT DOCUMENTS

| | | |
|---|---|---|
| WO | 2009/140948 A1 | 11/2009 |
| WO | 2010/120403 A2 | 10/2010 |
| WO | 2011/058641 A1 | 5/2011 |
| WO | 2013/049658 A1 | 4/2013 |
| WO | 2013/142777 A1 | 9/2013 |

OTHER PUBLICATIONS

Juan C. Moreno et al., "Design and implementation of an inertial measurement unit for control of artificial limbs: Application on legs orthoses", Sensors and Actuators B, Oct. 25, 2006, vol. 118, Nos. 1-2, pp. 333-337.

T. Suga et al., "Newly designed computer controlled knee-ankle-foot orthosis (Intelligent Orthosis)", 1998, Prosthetics and Orthotics International, vol. 22, No. 3, pp. 230-239.

J. Moreno et al., "Una aproximacion a la compensación y valoración funcional de marcha humana", Apr. 7, 2015 (with English translation).

\* cited by examiner

SYSTEM TO ASSIST WALKING

TECHNICAL FIELD OF THE INVENTION

The present invention relates to a gait assistance device for people with spinal cord injury who preserve hip flexion capacity. In particular, it relates to an active orthosis for gait assistance, by means of actuation of the knee and inertial sensing, for people with spinal cord injury who preserve hip flexion capacity. Moreover, the gait assistance device of the present invention can also be used to assist people, who preserve hip flexion capacity, suffering from stroke, traumatic brain injury, multiple sclerosis, cerebral palsy and poliomyelitis affecting lower limbs.

BACKGROUND OF THE INVENTION

A considerable number of people with spinal cord injury maintain certain control over the hip joint, but not the knee or ankle joint. These patients can walk using crutches and passive orthoses (Knee-Ankle-Foot Orthosis or KAFO) which block the rotation of the knee and limit plantar flexion of the ankle. The problem with this type of gait is that since the knee is always completely extended, there is a need to lift the hip in an unnatural manner to take a step, which entails a very high energy cost, leading patients to use a wheelchair in their daily life.

In a natural gait, flexion of the knee allows lowering the hip during the swing phase, which reduces oscillations of the center of mass, improving the energy efficiency of the gait. The use of a device which makes said flexion of the knee easier would lead people with spinal cord injury to be inclined to walk more instead of using a wheelchair, with the benefits that this would entail for their rehabilitation and health.

There are some active devices on the market, such as C-Brace by Otto Bock, which regulate knee joint stiffness depending on the reading from an inertial sensor measuring leg orientation and a force sensor measuring the reaction upon contact of the foot with the ground (see patent documents U.S. Pat. No. 8,876,912 B2 and US 2010/0125229 A1). The control system blocks the knee in the supporting phase and releases it during the swing phase. However, this device is not intended for use by people with spinal cord injury, but rather patients with a certain capacity to walk with no help, generally with a unilateral lesion. Patent document U.S. Pat. No. 7,985,193 B2 relates to a similar stiffness control device, but plantar sensors are not specified.

There is also another more generic patent document relating to a prosthesis which controls a joint by means of an actuator controlled based on the reading from a sensor (WO 2010/120403 A2), but it only refers to prosthetic devices.

For people with spinal cord injury, even those who have no control over the hip joint, there are exoskeletons for gait assistance such as ReWalk (ReWalk Robotics Ltd, Israel), Ekso GT (Ekso Bionics, USA), HAL (Cyberdyne Inc, Japan), Exo-H2 (Technaid SL, Spain), etc. They are large and very expensive devices that act on the ankle, knee and/or hip joints by means of electric motors or functional electrical stimulation.

BRIEF DESCRIPTION OF THE INVENTION

The present invention relates to a gait assistance system for people with spinal cord injury that preserve hip flexion capacity, solving the problems and limitations of the state of the art. Moreover, the gait assistance device of the present invention can also be used to assist people, who preserve hip flexion capacity, suffering from stroke, traumatic brain injury, multiple sclerosis, cerebral palsy and poliomyelitis affecting lower limbs.

The gait assistance device of the present invention can be used to assist walking in people suffering from the above cited diseases, without the need of a specific adaptation for the individual diseases.

More particularly it relates to a system to assist walking including at least a first orthosis for the leg of the user, where said orthosis has a support for the foot, a lower structure for the calf, an upper structure for the thigh, a lower articulation between the lower structure and the support for the foot. It also has an upper articulation between the lower structure and the upper structure. This system further incorporates an array of sensors for measuring at least the following variables:

- the angle of inclination ($\theta$) between the lower structure and the vertical,
- the angle of flexion ($\alpha_r$) between the lower structure and the upper structure, and
- the vertical acceleration of a point of the lower structure ($\alpha_z$).

This system also includes an actuator coupled to the upper articulation for setting the angle of flexion ($\alpha_r$) when it is activated by a control unit. Said control unit detects the need to apply a subsequent leg flexion-extension cycle according to the values measured by the preceding sensors. Said flexion-extension cycle is applied by changing the angle of flexion ($\alpha_r$) with the actuator of the upper articulation (knee).

Optionally, the plurality of sensors includes a uniaxial gyroscope and at least two uniaxial accelerometers.

Preferably, the system includes a second orthosis for the opposite leg of the user.

Optionally, the control unit can detect a subsequent leg flexion-extension cycle depending on the values measured by the sensors of the opposite leg.

Optionally, the control unit can detect a subsequent leg flexion-extension cycle when the vertical acceleration ($\alpha_z$) of said leg increases above a threshold.

Optionally, the control unit can detect a subsequent leg flexion-extension cycle when the vertical acceleration ($\alpha_z$) of the opposite leg remains below a threshold for a period of time.

Optionally, the control unit can detect a subsequent leg flexion-extension cycle depending on the angular velocity of the opposite leg.

Optionally, the actuator associated with the upper articulation can apply a variable angle depending on time during a flexion-extension cycle.

Optionally, the array of sensors for measuring the position of the leg includes at least one uniaxial gyroscope and two uniaxial accelerometers.

Optionally, the flexion-extension cycle is set and started when intention to walk is detected from the data of the array of sensors.

Optionally, the flexion of the knee is defined in each instant depending on the inclination of the opposite leg, or on the angular velocity of the opposite leg.

In a preferred embodiment, the present invention refers to the use of the system to assist walking, as defined above, in people who preserve hip flexion capacity suffering from spinal cord injury, stroke, traumatic brain injury, multiple sclerosis, cerebral palsy and poliomyelitis affecting lower limbs.

In another preferred embodiment, the present invention refers to a system to assist walking in people who preserve hip flexion capacity suffering from spinal cord injury, stroke, traumatic brain injury, multiple sclerosis, cerebral palsy and poliomyelitis affecting lower limbs, the system comprising:
- at least a first orthosis for a user's leg, where said orthosis comprises a support for the foot (1), a lower structure (2) for the calf, an upper structure (3) for the thigh, a lower articulation (4) between the lower structure (2) and the support for the foot (1), and an upper articulation (5) between the lower structure (2) and the upper structure (3);

characterized in that it further comprises:
- a plurality of sensors (6) configured for measuring at least:
  - the angle of inclination ($\theta$) between the lower structure (2) and the vertical,
  - the angle of flexion ($\alpha_r$) between the lower structure (2) and upper structure (3), and
  - the vertical acceleration ($\alpha_z$);
- an actuator coupled to the upper articulation (5) and configured for setting the angle of flexion ($\alpha_r$);
- a control unit (7) configured for detecting a subsequent leg flexion-extension cycle depending on the values measured by the sensors (6) and for applying said flexion-extension cycle by means of the variation of the angle of flexion ($\alpha_r$) through the actuator of the upper articulation (5).

BRIEF DESCRIPTION OF THE DRAWINGS

Some embodiments of the invention will be described below by way of non-limiting example in reference to the attached drawings, in which.

DETAILED DESCRIPTION OF THE INVENTION

Figure 1:
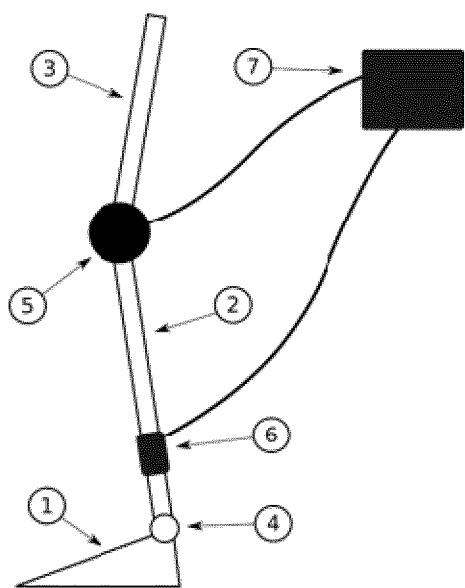
FIG. 1 schematically depicts an active orthosis.

A device, which is an embodiment of the invention, can be seen in FIG. 1. The device includes a pair of KAFO-type orthoses to which there is coupled an actuator for setting the angle of flexion ($\alpha_r$) of the knee, a sensor for measuring the angle of inclination ($\theta$) of the leg and optionally its vertical acceleration $\alpha_z$, a control unit (7) to which there are connected the array of sensors (6) and the actuator (5), the control unit (7) implements an algorithm to decide how to change the angle of the knee in the supporting phase (knee blocked) and swing phase (flexion-extension) depending on the reading from the sensors. This algorithm is explained in detail in FIG. 3.

Again, FIG. 1 shows an embodiment in which the main elements can be seen. A support (1) for the foot which can be rigid or flexible (often referred to as a "drop foot splint") and holds the user's foot, a rigid lower structure (2) which is secured to the patient's calf, a rigid upper structure (3) which is secured to the patient's thigh, a lower articulation (4) for the ankle, between elements (1) and (2), an upper articulation (5) for the knee allowing flexion between elements (3) and (2) and including an actuator coupled for applying an angle on the knee transmitting torque between structures (2) and (3), and an array of sensors (6) anchored to the element (2) for measuring the inclination and acceleration thereof. The data is processed by a control unit (7) for applying a movement on the upper articulation (5) through its associated actuator. The array of sensors (6) includes at least one uniaxial gyroscope and two uniaxial accelerometers for knowing in each instant the angle the leg forms with the ground, as well as the vertical acceleration.

Figure 2A:
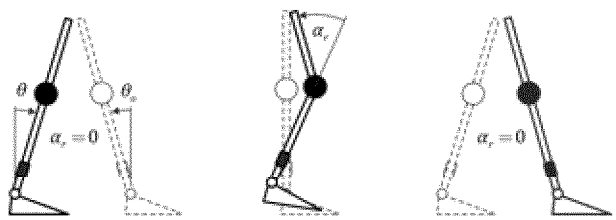
FIG. 2A depicts several positions adopted by the orthosis for walking.
Figure 2B:
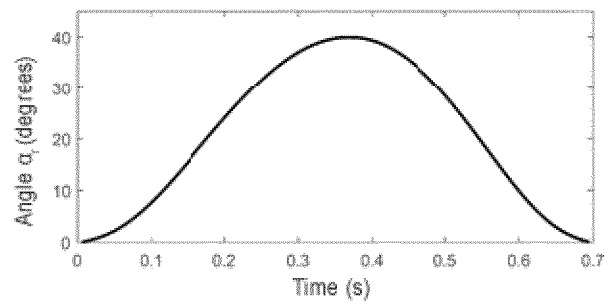
FIG. 2B shows a graph depicting the angle of the knee versus time for a possible flexion-extension cycle.

FIG. 2A shows different positions adopted by the orthosis while walking. FIG. 2B shows a graph of the angle formed by the knee $\alpha_r$ associated with the positions of FIG. 2A: flexion occurs in the left half; the corresponding extension occurs in the right half. Therefore, the angle $\alpha_r$ of 0 degree corresponds to the fully extended knee; the flexion of the knee reaches up to 40 degrees and is followed by a full extension (0 degrees). The solid line in FIG. 2A shows the right leg flexion-extension cycle, while the left leg, which is shown with a broken line, is supported and fully extended (blocked). It must be pointed out that the cycles, in this specific embodiment, would follow a pre-determined curve that depends on time.

As can be seen in FIG. 2B, the angle of the left leg increases monotonically when swinging the right leg, such that it can be used as an input to define the cycle in other embodiments of the present invention, as will be explained below.

In a second embodiment, the system would be installed in two orthoses, one for each leg. Each orthosis has its own actuator (5) and array of sensors (6) that are connected to a control unit (7). Therefore, for each leg, information both from its own sensors and the sensors of the opposite leg can be used, if necessary. The possibility of using the data from the sensors of one limb for controlling the opposite limb can serve to improve the interpretation of the data from the sensors. It is therefore considered that the cycle depends on the state of the opposite leg, whereby the angle $\alpha_r$ of the right knee would be dynamically defined based on the progression of the left leg (inclination and/or speed of rotation).

In one variant of the invention, flexion with a specific pace can be implemented in the actual actuator of the upper articulation (5) (corresponding to the knee) to adapt it to the desired gait by flexing/extending, once a cycle has been detected. In that case, the actuator incorporates a controller so that the motors determine a preset path (e.g., according to a time history of the flexion-extension of the knee).

Optionally, the desired flexion/extension characteristics can be established according to user preferences, so it may follow a curve different from that shown in FIGS. 2A-2B which the actuator would apply on the upper articulation (5) while walking, generally when the foot that is farther behind is lifted off the ground, such that the knee flexes while the leg swings. In order to detect the instant that is suitable for starting the flexion-extension cycle, the system preferably uses the array of sensors assembled in both legs, such that the cycle is only started on one leg if:
  a) First, the vertical acceleration has remained within a standby threshold for a minimum time.
  b) Then, the upward vertical acceleration exceeds a trigger threshold, and therefore it is interpreted that the foot is being lifted.
  c) Furthermore, the leg has at least one minimum forward inclination $\theta$.
  d) Meanwhile, the opposite leg exceeds a minimum backward inclination $\theta_o$.

With these verifications, safety ranges can be established to prevent a cycle from being started when the user does not actually have any intention to walk.

Figure 3:
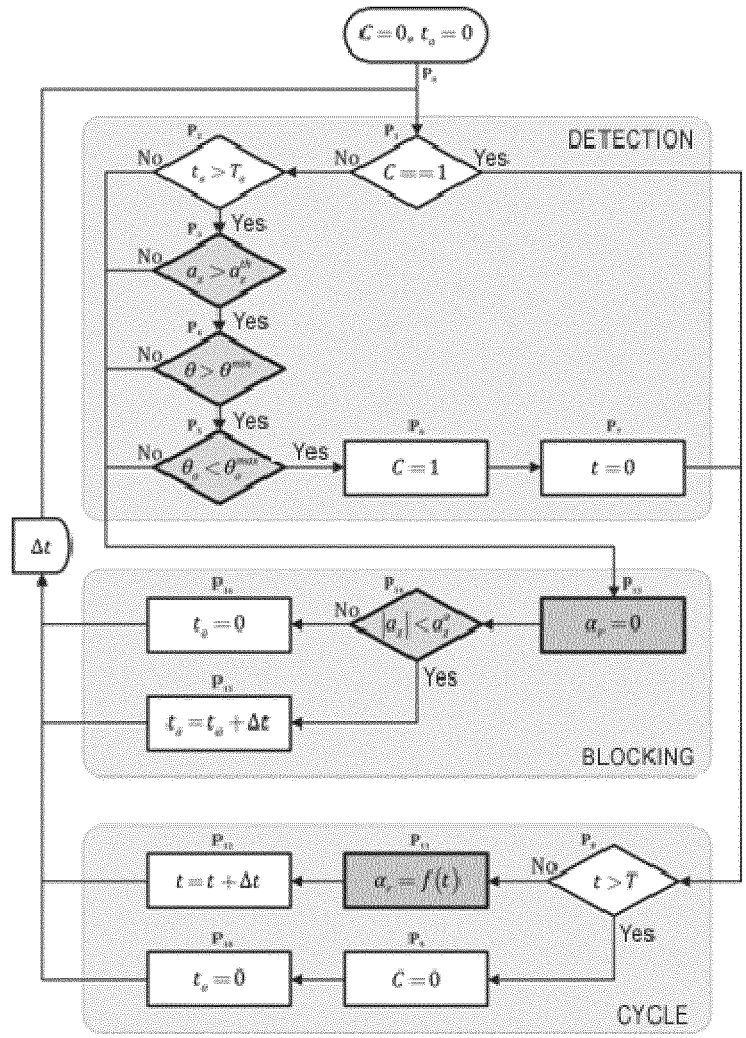
FIG. 3 shows a flow diagram followed by the control unit.

FIG. 3 describes in detail a control algorithm which the control unit (7) can implement and which can consider additional variables, such as angular velocity, also provided by the array of sensors (6). Robustness is therefore increased as the intention of the user to walk is detected.

The main steps carried out to decide, among others, on the moment in which the cycle must be started is explained in further detail in the following paragraphs. Variables are initialized in a first step (P0). As soon as the user lifts his/her heel, an upward vertical acceleration $\alpha_z$ which is captured by the accelerometer is produced. If it exceeds an activation threshold $\alpha_z^{th}$ (P3), it is considered that the heel is being lifted, and in principle the flexion-extension cycle would be started.

A problem related to the foregoing is that this acceleration is not only exceeded upon lifting the heel, but can also occur during the swing and/or in the moment the heel hits the ground after taking a step. To avoid drawing the wrong conclusion, the condition whereby the foot must have first been supported for a minimum time $T_\alpha$ (P2) before exceeding the minimum acceleration can be imposed. The condition of being supported is confirmed by verifying (P14) that the vertical acceleration value remains within a range of standby acceleration $\pm \alpha_z^\alpha$.

Additionally, for even greater certainty compliance with two other additional conditions can be established at the moment of detection: the angle of inclination of the right leg ($\theta$ in FIG. 2A, forward positive) must be greater than a preset value $\theta^{min}$ (P4), and the angle of inclination of the left leg ($\theta_o$ in FIG. 2A, also forward positive) must be less than a value $\theta_o^{max}$ (P5), which usually represents a backward inclination.

It is highly unlikely that the cycle will start incorrectly when these conditions are complied with. For example, if acceleration occurs in the right leg, the subject must adopt a posture similar to that shown on the left side of FIG. 2A so that the cycle is started, with the right leg inclined forward and the left leg inclined backward. This means that flexion of the knee does not occur when the foot is lifted with the legs parallel to one another (for example, when turning around), or if an acceleration occurs for any reason in the supported leg.

Another example of an elevated acceleration is when the heel hits the ground, but this will not start a cycle either. This is because the foot has not been previously in standby (P2, P14) as it comes from a swing phase, and furthermore the inclinations of the legs do not comply with the conditions (P4, P5), since the leg experiencing acceleration is farther ahead, and therefore inclined backward.

These and other verifications are described in the diagram of FIG. 3. The algorithm depicted therein is used by the control unit (7) to control the suitable operation of the flexion-extension cycles.

The gray (rhombus-shaped) decision blocks indicate measurements of the sensors, whereas the gray (rectangular) action blocks represent commands sent to the actuator (5).

The steps defined by the algorithm of FIG. 3 are run in a loop in the control unit (7), with a time step $\Delta t$, and there is imposed in each turn an angle of flexion $\alpha_r$ of the knee, which can be 0 in the blocking phase (P13), or a time function $f(t)$ in the swing phase (P11) which can be similar to the graph of FIG. 2B.

The variables shown in the diagram are as follows:
Variables representing the state of the system:
  C: indicates if the cycle (C=1) is under way or the leg is blocked (C=0).
  t: time elapsed from the start of the cycle.
  $t_\alpha$: time the foot has been supported.

Variables representing measurements of the sensors:
  $\alpha_z$: vertical acceleration measured by the accelerometer.
  $\theta$: angle between the leg and the vertical (forward positive).
  $\theta_o$: angle between the opposite leg and the vertical (forward positive).

Adjustable parameters:
  $\alpha_z^{th}$: upward acceleration that must be exceeded to start the cycle.
  $\alpha_z^\alpha$: maximum acceleration to consider that it is in standby.
  T: duration of the flexion-extension cycle (0.7 s in the example of FIG. 2B).
  $T_\alpha$: prior minimum standby time to enable starting the cycle.
  $\theta^{min}$: minimum angle of forward inclination for starting the cycle.
  $\theta_o^{max}$: maximum inclination of the opposite leg for starting the cycle.

Note: positive inclination is always a forward inclination. Therefore, the parameter $\theta_o^{max}$ will generally have a negative value.

The orthosis is preferably fixed by means of belts. Velcro is used in the upper and lower parts, and a support fastened with buckles can be placed on the knee.

Although cases with two orthoses were mentioned for an alternative embodiment, it may be sufficient for the user to use only one orthosis. The system would therefore only have information from an inertial sensor unit.

In another embodiment, the safety could be additionally increased by measuring the stress supported by the orthosis braces (canes), for example the measurement provided by a sensor, such as a strain gauge bridge.

REFERENCE NUMBERS IN THE DRAWINGS

1 Support for the foot.
2 Lower structure.
3 Upper structure.
4 Lower articulation.
5 Upper articulation.
6 Array of sensors.
7 Control unit.
P0 Initializing variables.
P1 Verifying whether the cycle is activated.
P2 Verifying the time the leg is in standby.
P3 Verifying the vertical acceleration of the leg.
P4 Verifying the angle of the leg with respect to the vertical.
P5 Verifying the angle of the opposite leg with respect to the vertical.
P6 Establishing the start of the cycle.
P7 Initializing the cycle time counter.
P8 Verifying the time from the beginning of the last cycle.
P9 Establishing the end of the cycle.
P10 Initializing the support time counter.
P11 Establishing the angle of the knee as a function of time.
P12 Increasing the cycle time counter.
P13 Establishing the angle of the blocked knee.
P14 Verifying the acceleration of the supported leg.
P15 Increasing the support time counter.
P16 Restarting the support time counter.

Several particular embodiments have been described in the present detailed description, but a person skilled in the art will be able to introduce modifications and replace technical features with other equivalent or improved features, depending on the requirements of each case, without departing from the scope of protection defined by the attached claims.

The invention claimed is:
1. A system to assist walking, comprising:
a first orthosis for a user's first leg and a second orthosis for the user's second leg, where the first and second orthoses each comprise:
  a support for a foot, a lower structure for a calf, an upper structure for a thigh, a lower articulation between the lower structure and the support for the foot, and an upper articulation between the lower structure and the upper structure;
  a plurality of sensors configured for measuring at least:
    an angle of inclination ($\theta$) between the lower structure and vertical;
    an angle of flexion ($\alpha\_r$) between the lower structure and upper structure; and
    a vertical acceleration ($a\_z$); and
  an actuator coupled to the upper articulation and configured for setting the angle of flexion ($\alpha\_r$); and
a control unit configured for detecting a subsequent leg flexion-extension cycle depending on values measured by the sensors and for applying said flexion-extension cycle by variation of the angle of flexion ($\alpha\_r$) through the actuators of the upper articulations;
wherein the control unit is configured for detecting a subsequent leg flexion-extension cycle when the following conditions are complied with:
  first, the vertical acceleration of the first leg has remained within a standby threshold for a first period of time,
  then, the vertical acceleration of the first leg increases above a threshold for a second period of time, and
  the angle of inclination of the first leg is greater than a first preset value, and the angle of inclination of the second leg is less than a second preset value.

2. The system to assist walking according to claim 1, where the plurality of sensors comprises a uniaxial gyroscope and at least two uniaxial accelerometers.

3. The system to assist walking according to claim 1 where the control unit is configured for detecting a subsequent leg flexion-extension cycle when the vertical acceleration ($a\_z$) of the second leg remains below a threshold for a period of time.

4. The system to assist walking according to claim 1, where the control unit is configured for detecting a subsequent leg flexion-extension cycle depending on the angular velocity of the second leg.

5. The system to assist walking according to claim 1, where the actuator associated with the upper articulation is configured for applying a variable angle depending on time during a flexion-extension cycle.

6. Using a system, the system comprising:
a first orthosis for a user's first leg and a second orthosis for the user's second leg, where the first and second orthoses each comprise:
  a support for a foot of the user, a lower structure for a calf of the user, an upper structure for a thigh of the user, a lower articulation between the lower structure and the support for the foot, and an upper articulation between the lower structure and the upper structure;
  a plurality of sensors configured for measuring at least:
    an angle of inclination ($\theta$) between the lower structure and vertical;
    an angle of flexion ($\alpha\_r$) between the lower structure and upper structure; and
    a vertical acceleration ($a\_z$); and
  an actuator coupled to the upper articulation and configured for setting the angle of flexion ($\alpha\_r$); and
a control unit configured for detecting a subsequent leg flexion-extension cycle depending on values measured by the sensors and for applying said flexion-extension cycle by variation of the angle of flexion ($\alpha\_r$) through the actuators of the upper articulations;
wherein the control unit is configured for detecting a subsequent leg flexion-extension cycle when the following conditions are complied with:
  first, the vertical acceleration of the first leg has remained within a standby threshold for a first period of time,
  then, the vertical acceleration of the first leg increases above a threshold for a second period of time, and
  the angle of inclination of the first leg is greater than a first preset value, and the angle of inclination of the second leg is less than a second preset value;
the using comprising:
securing the first orthosis to the user's first leg and the second orthosis to the user's second leg, each by holding the user's foot with the support, securing the lower structure to the user's calf, and securing the upper structure to the user's thigh; and
using the system to assist walking of the user, the user preserving hip flexion capacity and suffering from spinal cord injury, stroke, traumatic brain injury, multiple sclerosis, cerebral palsy or poliomyelitis affecting lower limbs.

7. A system to assist walking in people who preserve hip flexion capacity suffering from spinal cord injury, stroke, traumatic brain injury, multiple sclerosis, cerebral palsy and poliomyelitis affecting lower limbs, the system comprising:
a first orthosis for a user's first leg and a second orthosis for the user's second leg, where the first and second orthoses each comprise:
  a support for a foot, a lower structure for a calf, an upper structure for a thigh, a lower articulation between the lower structure and the support for the foot, and an upper articulation between the lower structure and the upper structure;
  a plurality of sensors configured for measuring at least:
    an angle of inclination ($\theta$) between the lower structure and vertical;
    an angle of flexion ($\alpha\_r$) between the lower structure and upper structure; and
    a vertical acceleration ($a\_z$); and
  an actuator coupled to the upper articulation and configured for setting the angle of flexion ($\alpha\_r$); and
a control unit configured for detecting a subsequent leg flexion-extension cycle depending on values measured by the sensors and for applying said flexion-extension cycle by variation of the angle of flexion ($\alpha\_r$) through the actuators of the upper articulations;
wherein the control unit is configured for detecting a subsequent leg flexion-extension cycle when the following conditions are complied with:
  first, the vertical acceleration of the first leg has remained within a standby threshold for a first period of time,
  then, the vertical acceleration of the first leg increases above a threshold for a second period of time, and
  the angle of inclination of the first leg is greater than a first preset value, and the angle of inclination of the second leg is less than a second preset value.

* * * * *